(12) United States Patent
Cummins et al.

(10) Patent No.: US 10,105,247 B2
(45) Date of Patent: Oct. 23, 2018

(54) THUMBWHEEL ACTUATED VASCULAR INTERVENTION DEVICE DELIVERY SYSTEM

(71) Applicant: Cook Medical Technologies LLC, Bloomington, IN (US)

(72) Inventors: Sean Cummins, Limerick (IE); Darach McGrath, Tipperary (IE); Olivia Ryan, Co. Clare (IE); James Butler, Co. Tipperary (IE); Joe Hayes, Co. Clare (IE)

(73) Assignee: Cook Medical Technologies LLC, Bloomington, IN (US)

( * ) Notice: Subject to any disclaimer, the term of this patent is extended or adjusted under 35 U.S.C. 154(b) by 312 days.

(21) Appl. No.: 14/825,631

(22) Filed: Aug. 13, 2015

(65) Prior Publication Data

US 2016/0074191 A1 Mar. 17, 2016

Related U.S. Application Data

(60) Provisional application No. 62/050,388, filed on Sep. 15, 2014.

(51) Int. Cl.
*A61F 2/966* (2013.01)
*A61F 2/95* (2013.01)
(Continued)

(52) U.S. Cl.
CPC ............. *A61F 2/95* (2013.01); *A61F 2/844* (2013.01); *A61F 2/962* (2013.01); *A61F 2/966* (2013.01);
(Continued)

(58) Field of Classification Search
CPC .................... A61F 2/95; A61F 2/966
See application file for complete search history.

(56) References Cited

U.S. PATENT DOCUMENTS 6,190,360 B1 2/2001 Iancea et al.
6,238,402 B1 5/2001 Sullivan, III et al.
(Continued)

FOREIGN PATENT DOCUMENTS

EP 2431009 3/2012
WO 2008034793 3/2008

OTHER PUBLICATIONS

Information Disclosure Statement and Declaration of Darach McGrath Re: ev3 Inc. Stent Delivery System On-Sale Jul. 11, 2013 Prior Art.

*Primary Examiner* — Julie A Szpira
(74) *Attorney, Agent, or Firm* — Liell & McNeil

(57) ABSTRACT

A vascular intervention device delivery system, such as for implanting a self expanding stent, includes a thumbwheel rotatably mounted in a handle. A catheter has a proximal end attached to the handle and a distal carrier segment for mounting a stent thereon. A retractable sheath is movable to a position retracted proximally to uncover the distal carrier segment. A pull with a curved cross section extends between the thumbwheel and the retractable sheath. An idler wheel with a perimeter notch is rotatably mounted in the handle proximal to the thumbwheel. A pin is movably in the handle between a first position received in the perimeter notch to block rotation of the idler wheel, and a second position outside of the perimeter notch to permit rotation of the idler wheel. The pull wraps around the idler wheel to return in a direction for being wound onto a spool of the thumbwheel.

20 Claims, 4 Drawing Sheets

(51) Int. Cl.
*A61F 2/962* (2013.01)
*A61F 2/844* (2013.01)
*A61B 17/00* (2006.01)

(52) U.S. Cl.
CPC ........... *A61B 2017/00407* (2013.01); *A61F 2002/9517* (2013.01); *A61F 2230/0069* (2013.01)

(56) References Cited

U.S. PATENT DOCUMENTS

| | | |
|---|---|---|
| 7,967,829 B2 | 6/2011 | Gunderson et al. |
| 7,976,574 B2 | 7/2011 | Papp |
| 8,025,692 B2 * | 9/2011 | Feeser ............... A61F 2/966 604/264 |
| 8,500,789 B2 | 8/2013 | Wuebbeling et al. |
| 2005/0149159 A1 | 7/2005 | Andreas et al. |
| 2005/0273151 A1 | 12/2005 | Fulkerson et al. |
| 2006/0259124 A1 | 11/2006 | Matsuoka et al. |
| 2007/0032860 A1 | 2/2007 | Brooks et al. |
| 2007/0055342 A1 | 3/2007 | Wu et al. |
| 2007/0088421 A1 | 4/2007 | Loewen |
| 2007/0156225 A1 | 7/2007 | George et al. |
| 2007/0168014 A1 | 7/2007 | Jimenez et al. |
| 2008/0091257 A1 | 4/2008 | Andreas et al. |
| 2009/0210046 A1 | 8/2009 | Shumer et al. |
| 2010/0004606 A1 * | 1/2010 | Hansen ............... A61F 2/95 604/264 |
| 2012/0041537 A1 | 2/2012 | Parker et al. |
| 2012/0059448 A1 | 3/2012 | Parker et al. |
| 2012/0101562 A1 | 4/2012 | Gunderson et al. |
| 2012/0116493 A1 * | 5/2012 | Harada ............... A61F 2/95 623/1.12 |
| 2012/0123516 A1 | 5/2012 | Gerdts et al. |
| 2012/0158120 A1 | 6/2012 | Hacker et al. |
| 2012/0330401 A1 | 12/2012 | Sugimoto et al. |
| 2013/0013047 A1 | 1/2013 | Ramos et al. |
| 2013/0018451 A1 | 1/2013 | Grabowski et al. |
| 2013/0110223 A1 | 5/2013 | Munsinger et al. |
| 2014/0188209 A1 | 7/2014 | Loewen |
| 2015/0297378 A1 | 10/2015 | Senness et al. |

* cited by examiner

THUMBWHEEL ACTUATED VASCULAR INTERVENTION DEVICE DELIVERY SYSTEM

TECHNICAL FIELD

The present disclosure relates generally to vascular intervention device delivery systems, and more particularly to features that support thumbwheel actuation for deployment of a vascular intervention device.

BACKGROUND

Self expanding stents and similar vascular intervention devices are often delivered and deployed using so called pin and pull systems. Typically, the stent is compressed between a retractable outer sheath and an inner catheter. To deploy the stent, the user has to pull the outer sheath to uncover the stent using one hand while resisting the force with the other hand on the inner catheter to maintain the position of the stent during deployment. In pin and pull systems, the user can have difficulty maintaining the inner catheter at a fixed position while simultaneously moving the outer sheath. In very difficult stent deployments, which require a large amount of force by the user, this simultaneous push and pull may lead to inaccurate stent positioning, shortening or lengthening of the stent, or possibly even damage to the stent or target vessel. Another disadvantage of pin and pull systems is that there can be a lack of control on the deployment because the force to deploy the stent decreases as more of the stent is deployed. If the user maintains the same high force during deployment, the stent may be deployed too fast for the user to control. Another potential problem relates to building up tension in the outer sheath prior to movements thereof during the deployment process. If the user pauses during the deployment and releases this built up tension, deployment errors can occur when the user resumes tension to again move the outer sheath to the deployment position fully uncovering the self explaining stent. Another occasional problem relates to early partial deployment of a stent due to friction on the retractable sheath en route to a delivery site.

The present disclosure is directed toward one or more of the problems set forth above.

SUMMARY OF THE DISCLOSURE

A vascular intervention device delivery system includes a thumbwheel mounted in a handle. The thumbwheel has a spool and a radially outward thumb surface. A catheter has a proximal end attached to the handle, and a distal carrier segment for mounting a vascular invention device thereon. A retractable sheath is movable from a first position covering the distal carrier segment to a second position retracted proximally uncovering the distal carrier segment. A pull extends between the thumbwheel and the retractable sheath. The pull has a cross sectional shape with a concave side that is opposite to a convex side. An idler wheel is rotatably mounted in the handle at a location proximal to the thumbwheel. The pull wraps around the idler wheel to return in a direction for being wound onto the spool of the thumbwheel.

In another aspect, a vascular intervention device delivery system includes a thumbwheel rotatably mounted in a handle. The thumbwheel includes a spool and a radially outward thumb surface. A catheter has a proximal end attached to the handle and a distal carrier segment for mounting a vascular intervention device thereon. A retractable sheath is movable from a first position covering the distal carrier segment to a second position retracted proximally uncovering the distal carrier segment. A pull extends between the thumbwheel and the retractable sheath. An idler wheel is rotatably mounted in the handle at a location proximal to the thumbwheel. The idler wheel defines a perimeter notch. A pin is movably mounted in the handle, and is movable between a first position at which the pin is received in the perimeter notch to block rotation of the idler wheel, and a second position outside of the perimeter notch to permit rotation of the idler wheel. The pull wraps around the idler wheel to return in a direction for being wound onto the spool of the thumbwheel.

In still another aspect, a method of operating a vascular intervention device delivery system includes inhibiting movement of the retractable sheath toward the second position while a distal end of the vascular intervention device delivery system is being maneuvered to a delivery site at least in part by contacting the pull with a pin mounted in the handle. The pin is moved out of contact with the pull when the distal end arrives at the delivery site. The retractable sheath is moved from the first position to the second position responsive to rotation of the thumbwheel in a reverse direction.

DETAILED DESCRIPTION

Figure 1:
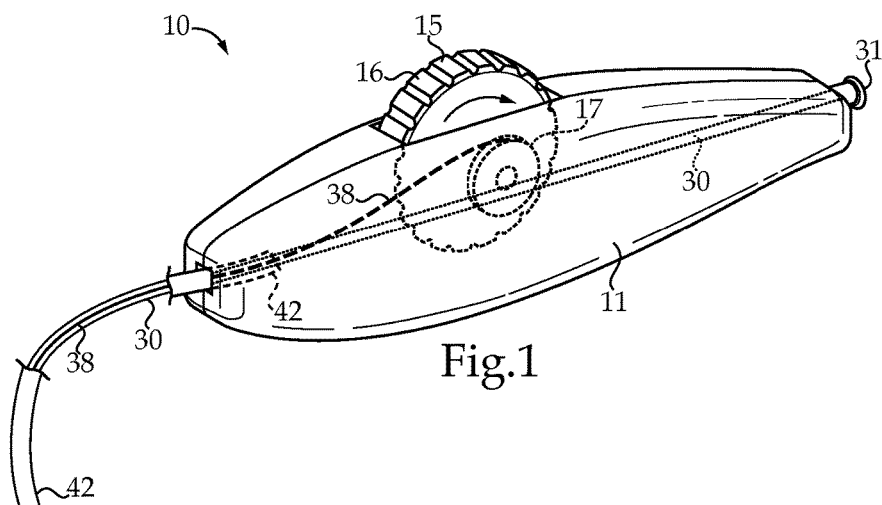
FIG. 1 is a perspective schematic view of a vascular intervention device delivery system according to the present disclosure.
Figure 2:
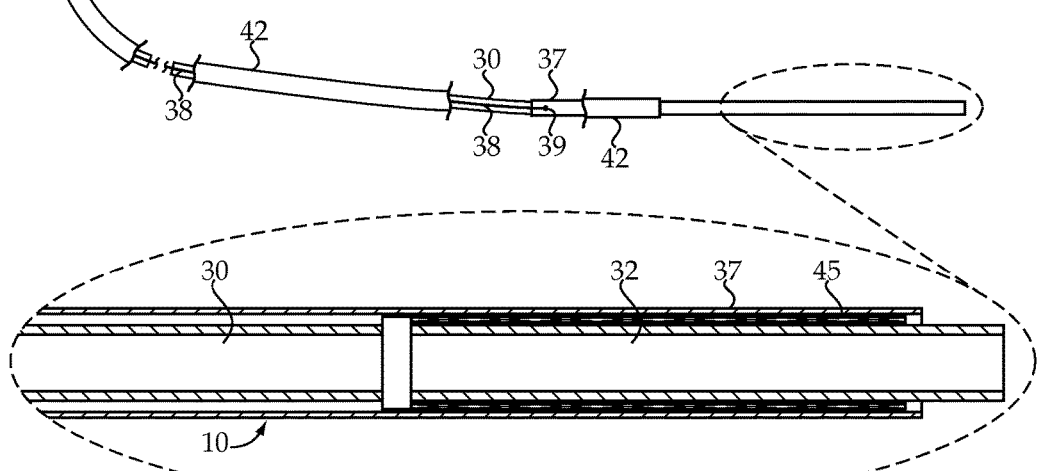
FIG. 2 is an enlarged view of the distal segment of the delivery system shown outlined with a dashed line in FIG. 1.
Figure 3:
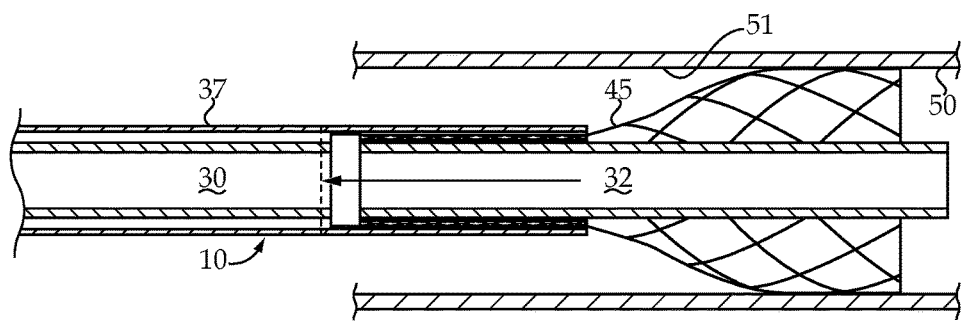
FIG. 3 is a view similar to FIG. 2 about half way through a deployment of a self expanding stent.

Referring to FIGS. 1-3, a vascular intervention device delivery system 10 is shown before and during delivery of a self expanding stent 45 at a delivery site 51 in the vessel 50 of a patient. Delivery system 10 includes a handle 11 that may be gripped in one hand by a user during a delivery procedure. Handle 11 may be manufactured from a suitable molded plastic, such as in two longitudinal halves that are joined in any suitable manner to form the complete handle 11. A thumbwheel 15 is rotatably mounted in the handle 11 and has a radially outward thumb surface 16 and a spool 17. A catheter 30 has a proximal end 31 attached to handle 11, and a distal carrier segment 32 for mounting a vascular intervention device, such as a self expanding stent 45, thereon. Proximal end 31 may take the form a Luer lock fitting to receive a wire guide, or so that treatment fluids or the like may be injected through catheter 30 in a manner well known in the art. A retractable sheath 37 is movable with respect to catheter 30 from a first position covering the distal carrier segment 32 to a second position indicated by the dashed line in FIG. 3 at which the retractable sheath 37 has been refracted proximally to uncover the distal carrier segment 32. FIG. 3 shows the retractable sheath 37 about half way between the first position and the second position.

A pull 38 extends between the spool 17 of thumbwheel 15 and the retractable sheath 37. Pull 38, which preferably is less elastic than the retractable sheath 37, may be attached to retractable sheath 37 at an attachment 39 in any manner known in the art, such as by welding pull 38 to a metallic reinforcement of retractable sheath 37. In most versions of the vascular intervention device delivery system 10 of the present disclosure, pull 38 will be longer than retractable sheath 37. Nevertheless, retractable sheath 37 could be longer than pull 38 without departing from the present disclosure. Pull 38 may comprise a metallic wire or thin band of metal, which may have a curved cross sectional shape.

A wire retention/stability sheath 42 surrounds a majority of the length of pull 38, and serves to keep pull 38 in close proximity to the outer surface of catheter 30 over much of the length of delivery system 10. Wire retention/stability sheath 42 may be unattached to catheter 30, pull 38 or retractable sheath 37, but may be attached to move with pull 38 and/or retractable sheath 37. On the other hand, wire retention/stability sheath 42 may be attached to catheter 30 at one or more locations so that pull 38 and retractable sheath 37 also move with respect to wire retention/stability sheath 42 during the delivery process. Wire retention/stability sheath 42 may terminate and be attached at its proximal end at a fixation point within handle 11.

When in its pre-deployment configuration, as shown in FIGS. 1 and 2, a vascular intervention device, such as a self expanding stent 45, is disposed between an outer surface of the distal carrier segment 32 of catheter 30, and an inner surface of the retractable sheath 37. During a typical procedure, the distal carrier segment 32 is positioned at a delivery site 51 within a vessel 50 of a patient. After achieving proper positioning, the user then grips handle 11 and begins to rotate thumbwheel 15 so that pull 38 is wound onto spool 17. As this occurs, pull 38 and retractable sheath 37 move proximally with respect to catheter 30 to allow the self expanding stent 45 to expand away from carrier segment 32 and into contact with the inner wall of vessel 50 in a manner well known in the art. During this process, catheter 30, or an outer catheter (not shown) that terminates adjacent stent 45, may be placed in compression while both pull 38 and retractable sheath 37 are in tension. According to the present disclosure, handle 11 and thumbwheel 15 include a structure that allows thumbwheel 15 to rotate to wind pull 38 onto spool 17, but prevent rotation in an opposite direction. This aspect of the disclosure allows the user to stop the deployment procedure while retaining the stored elastic energy in pull 38 and retractable sheath 37.

Figure 4:
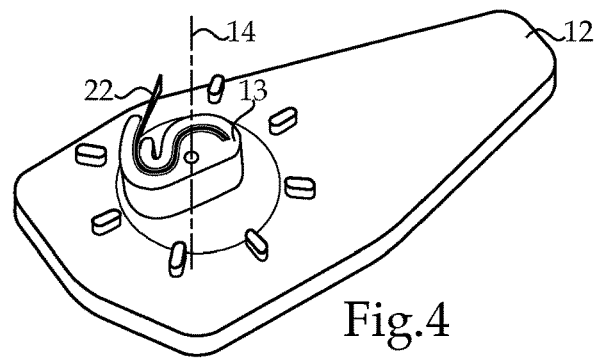
FIG. 4 is a perspective view of an assembly plate for the handle shown in FIG. 1.
Figure 5:
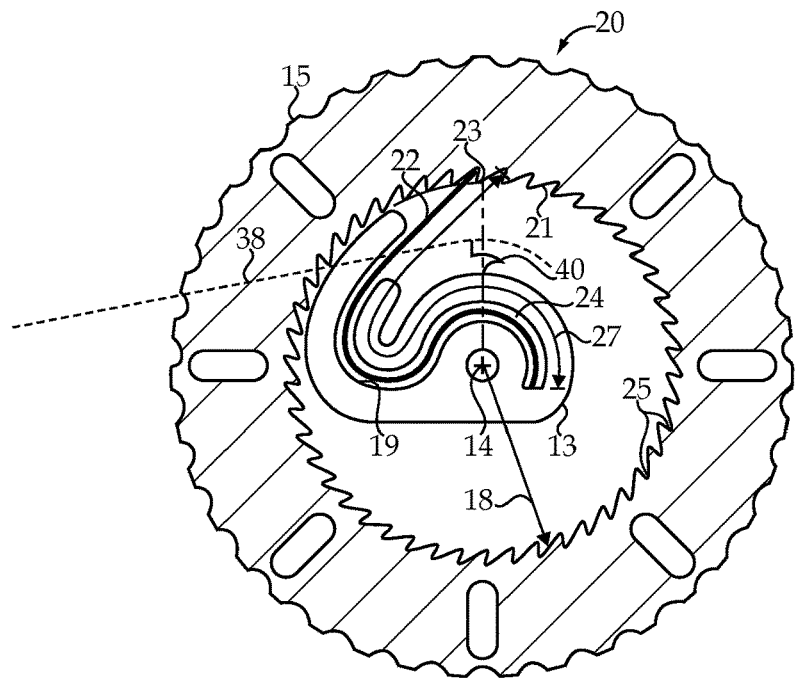
FIG. 5 is a partial sectioned view showing the ratchet according to the present disclosure.
Figure 6:
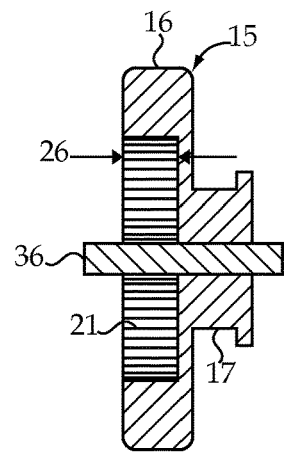
FIG. 6 is a sectioned side view through the thumbwheel of FIGS. 1 and 5.

Referring now in addition to FIGS. 4-6, a ratchet 20 provides the structure that prevents thumbwheel 15 from rotating in a forward direction. In particular, handle 11 may be formed to include, or have attached to an inner surface, an assembly plate 12 that defines a hub 13 that receives an axle 36 upon which thumbwheel 15 is rotatably mounted to rotate about axis 14 in a reverse direction permitted by ratchet 20. Thumbwheel 15 includes a radially inward ratchet surface 31 of ratchet 20. A ratchet pawl 22 of ratchet 20 is mounted in the handle 11, and has a catch 23 in contact with ratchet surface 21 of thumbwheel 15. Ratchet 20 holds thumbwheel 15 against rotation in a forward direction, but the retractable sheath 37 moves responsive to rotation of the thumbwheel 15 in a reverse direction.

In the illustrated embodiment, catch 23 takes the form of a deformed rectangular shaped band of spring steel 24 that is received in an S-shaped groove 19 defined by assembly plate 12 and oriented parallel to axis 14. The ratchet surface 21 of thumbwheel 15 may define a plurality of stops 25 in each of four 90° rotation angles. In the specific embodiment shown, ratchet surface 21 defines at least fifty stops 25 per revolution of thumbwheel 15 in order to provide the user with precise tactile control over the delivery procedure. The deformed band of spring steel 24 may have a width that contacts the ratchet surface 21 across the width 26. In addition, although not necessary, the deformed band of spring steel 24 may have a length 27 that is greater than radius 18 of thumbwheel 15. An imaginary line 40 that extends parallel from an end 28 of catch 23 to the axis 14 may be configured to be orthogonal to pull 38 where pull 38 contacts spool 37, as best shown in FIG. 5.

Referring now to FIGS. 7-11, a vascular intervention device delivery system 60 according to another aspect includes a ratchet 70 and a handle 61 with a structure that differs from that shown in relation to FIGS. 4-6. However, where similar numbers are used, those features correspond to similar features shown in FIGS. 1-3. Vascular intervention device delivery system 60 differs from the system 10 described earlier by, among other features, the shape and structure of the ratchet pawl 72 and by the inclusion of a lock 80. Like the earlier version, ratchet 70 provides a structure that prevents thumbwheel 66 from rotating in a forward direction.

Figure 7:
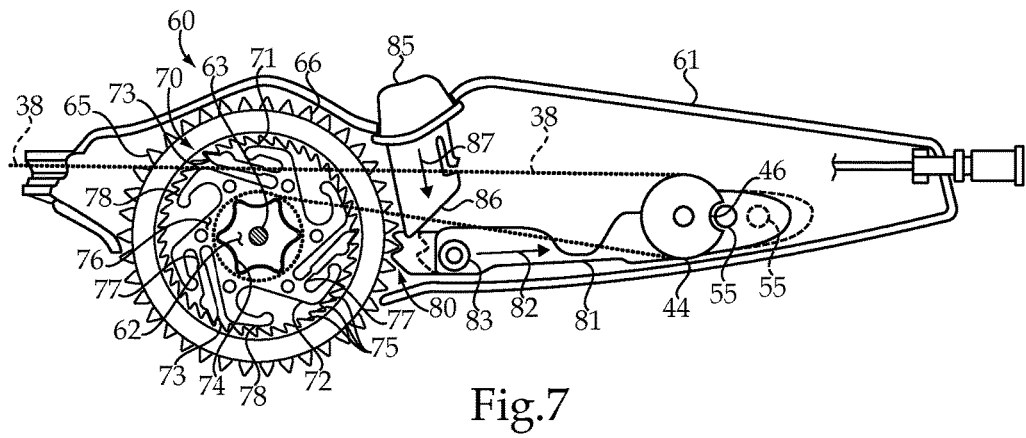
FIG. 7 is a sectioned side view of a handle portion of a vascular intervention device delivery system according to another aspect of the present disclosure.
Figure 8:
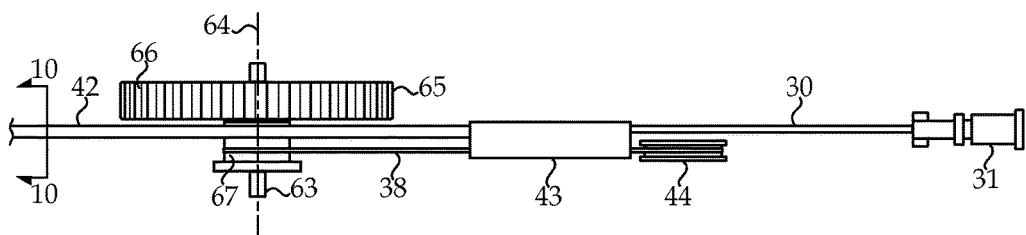
FIG. 8 is a top view of the inner workings of the vascular intervention device delivery system of FIG. 7, minus the handle.

Handle 61 may be formed from a suitable plastic to include a key shaped hub 62 that is received in a matching key shaped opening 74 defined by ratchet pawl 72. This configuration permits assembly of ratchet pawl 72 to key shaped hub 62 in a plurality of different but equivalent angular orientations. Key shaped hub 72 may define a central opening that receives an axle 63 to define an axis 64 about which thumbwheel 65 rotates. Thumbwheel 65 includes a radially outward thumb surface 66 and a radially inward ratchet surface 71. Thumbwheel 65 may also include a spool 67 upon which the pull 38 is wound when the device delivery system 60 is operated. In this version, the wire retention/stability sheath 42 terminates at a junction box 43 (not shown in FIG. 7 for the sake of clarity) positioned within handle 61. As in the previous version, the pull 38 is positioned within the wire retention/stability sheath 42 and emerges from the junction box 43 to wrap around an idler wheel 44 and return in a reverse direction for being wound onto spool 67 as best shown in FIGS. 7 and 8. Idler wheel 44 is rotatably mounted in handle 61 and positioned proximal to thumbwheel 65. As in the previous embodiment, ratchet 70 prevents thumbwheel 65 from rotating in a forward direction, but the retractable sheath 37 (FIGS. 1-3) moves responsive to rotation of thumbwheel 65 in a reverse direction.

In this embodiment, catch 73 takes the form of spiral arms 79 that are attached to a central body 76 by living hinges 77. Unlike the ratchet pawl 22 shown in the embodiment in FIGS. 4-6, ratchet pawl 72 may most conveniently be formed of a suitable plastic material. When thumbwheel 65 is rotated in a reverse direction, each of the three catches 73 will click and be received into respective stops 75 that define ratchet surface 71. In this embodiment, ratchet catches 73 are equally distributed 120° apart around the axis 64 defined by axle 63. Thus, the three catches 73 will simultaneously contact the ratchet surface 71 at three different locations located 120° apart about axis 64. Those skilled in the art will appreciate that a ratchet pawl 72 having two, four or more catches 73 would also fall within the intended scope of this disclosure.

Figure 9:
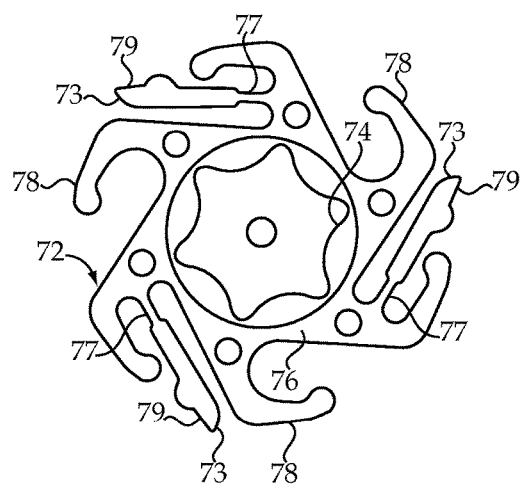
FIG. 9 is a side view of a ratchet pawl for the vascular intervention device delivery system of FIG. 7.

As best shown in FIGS. 7 and 9, the ratchet pawl 72 includes curved arms 78 that are distributed to provide a circular guide for the thumbwheel as the ratchet teeth rotate around the fixed ratchet. Thus, in some embodiments, the use of curved arms 78 could permit omission of axle 63 as shown, since the thumbwheel would rotate about axis 64 with the curved arms 78 contacting ratchet surface 71, even without the inclusion of axle 63. It is also worth noting that this embodiment differs from the earlier embodiment in that both the ratchet pawl 72 and the ratchet surface 71 of thumbwheel 65 may be made out of plastic, as opposed to a metal ratchet pawl 22 acting on a plastic ratchet surface 21 as in the earlier embodiment. By making both the pawl and the ratchet surface from the same material, the potential creation of the debris caused by the interaction of metal with plastic can be avoided.

In addition to ratchet 70, vascular intervention device delivery system 60 includes a lock 80 that allows thumbwheel 65 to be disabled during shipment and during positioning of the distal carrier segment 32 (FIGS. 1-3) at a delivery site 51 within a patient. The lock 80 is movable between a locked position, as shown, and an unlocked position shown in FIG. 11, and by dashed lines in FIG. 7. The lock 80 includes a latch 81 positioned in handle 61 and movable along a line 82 between the locked position at which the latch 81 engages and contacts the radially outward thumb surface 66 of thumbwheel 65, and the unlocked position at which the latch 81 is out of contact with the radially outward thumb surface 66. Lock 80 also includes a pusher 85 that is at least partially positioned outside of handle 61, but on an opposite side of handle 61 from the exposed portion of thumbwheel 65. The pusher may include a wedge 86 that engages a post 83 of latch 81. Post 83 may be oriented perpendicular to the line 82 of action of latch 81. Vascular intervention device delivery system may be enabled by depressing pusher 85 along line 87 to move latch 81 out of contact with radially outward thumb surface 66 of thumbwheel 65.

Figure 10:
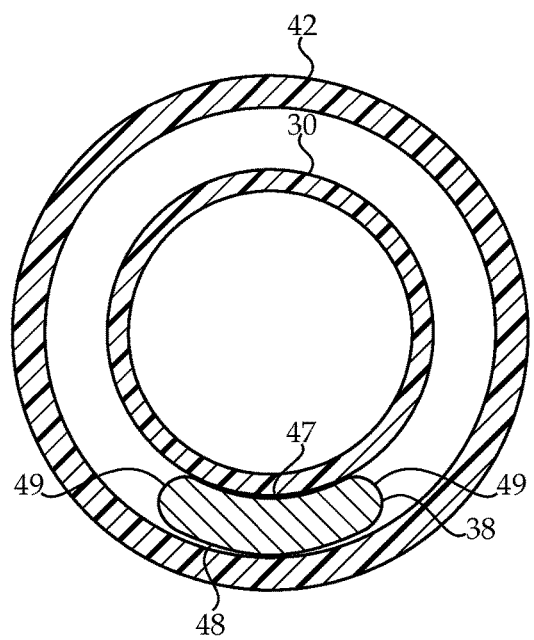
FIG. 10 is a sectioned view through a portion of the vascular intervention device delivery system as viewed along section lines 10-10 of FIG. 8.
Figure 11:
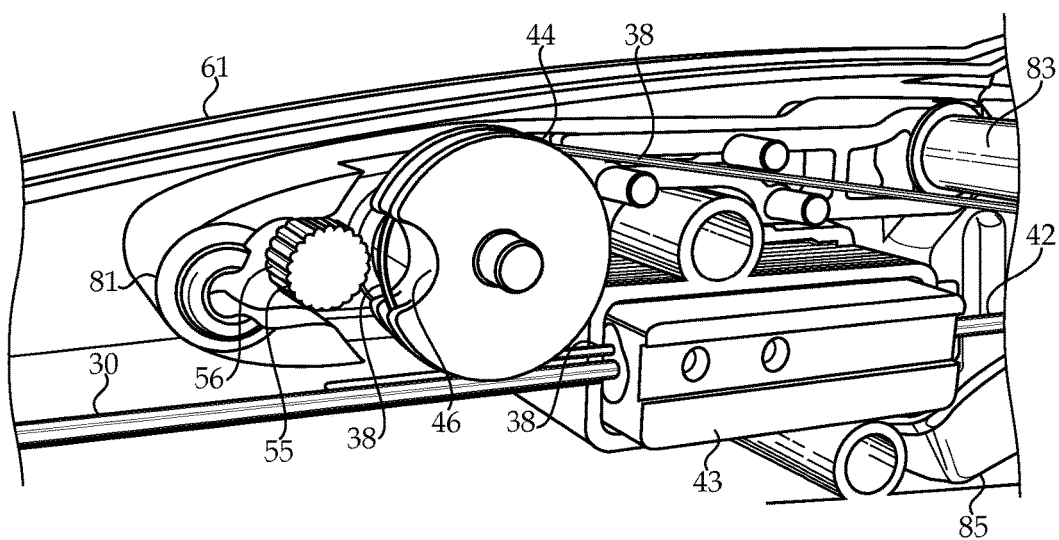
FIG. 11 is a partial perspective view of a portion of the handle from FIG. 7 that includes the idler wheel.

Referring in addition to FIGS. 10 and 11, pull 38 may have a curved cross section with a concave side 47 that is opposite to a convex side 48, both of which are flanked by rounded edges 49. The concave side 47 and the convex side 48 are the long sides of the pull 38 cross section. In the illustrated embodiment, the idler wheel 44 and the spool 67 are arranged so that the convex side 48 is in contact with idler wheel 48, and the concave side 47 is in contact with spool 67. Nevertheless, those skilled in the art will appreciate that the opposite configuration would also fall within the scope of the present disclosure. Pull 38 may be positioned between stability sheath 42 and catheter 30. As best shown in FIG. 10, the convex side 48 of pull 38 is in contact with the inner surface of stability sheath 42. The convex side 47 may be in contact with, or adjacent to, the outer surface of catheter 30. In order to reduce friction, and reduce the contact area between pull 38 and stability sheath 42 as well as catheter 30, the radius of convex side 48 may be smaller than the radius of the inner surface of stability sheath 42. Likewise, the radius of concave side 47 may be less than the outer radius of catheter 30. Pull 38 may be manufactured from a suitable band of spring steel to have the curved cross sectional shape shown in FIG. 10. Pull 38 may be made from stainless steel with a sufficiently large cross section that the pull does not stretch when in tension at expected magnitudes (10's of Newtons) during a delivery process. The curved cross sectional shape of pull 38 may provide columnar support to retractable sheath 37 while the distal carrier segment 32 is being maneuvered to delivery site 51.

Latch 81 not only moves between positions in contact and out of contact with thumbwheel 65, movement of lock 80 may also enable rotation of idler wheel 44. In particular, idler wheel 44 may define a perimeter notch 46. A pin 55 is mounted to move with latch 81 between a position in which pin 55 is received in perimeter notch 46 to block rotation of idler wheel 44, and a second position (FIG. 11) outside of perimeter notch 46 to permit rotation of idler wheel 44. Pin 55 may include a knurled surface 56 that is in contact with pull 38 when pin 55 is in the first position received in perimeter notch 46. The knurled surface 56 is out of contact with pull 38 in the second position as best shown in FIG. 11. Although pin 55 is shown as attached to a moving with latch 81, pin 55 could be mounted to move independently of latch 81 without departing from the intended scope of the present disclosure. When pin 55 is in the first position received in perimeter notch 46 and has its knurled surface 56 in contact with pull 38 as shown in FIG. 7, this interaction not only serves to prevent rotation of idler wheel 44, but also serves to provide columnar support for pull 38 to support against movement of retractable sheath 37 when the device is being maneuvered to a delivery site 51 within a patient. For instance, friction on retractable sheath 37 in the proximal direction during the maneuvering procedure is inhibited by the columnar strength provided by pull 38 and its contact with pin 55. Those skilled in the art might appreciate that the knurled surface 56 may help, but it is mostly believed to be the pressured applied by pin 55 onto the pull 38 that provides the columnar support when the two features are in contact. Other potential options in place of knurled surface 56 include but are not limited to a rubber overmold on pin 55 to create friction on pull 38, or pin 55 could have a splined surface or maybe even a rough/smooth finish without departing from the present disclosure.

INDUSTRIAL APPLICABILITY

The present disclosure is generally applicable to vascular intervention device delivery systems, and more particularly to a delivery system for delivery of self expanding stents and other vascular intervention devices with self expanding action. The present disclosure finds specific applicability to delivery of relatively long vascular intervention devices that produce substantial friction on the inner surface of retractable sheath 37, and thus require higher forces on retractable sheath 37 and pull 38 in order to successfully deliver the vascular intervention device to an intended treatment site.

The vascular intervention device delivery system 10, 60 will typically be packaged in a conventional sterile packaging in a known manner for shipment. After a wire guide (not shown) has been positioned in a patient's body across a treatment location, the catheter 30 may be slid over the wire guide to position the distal carrier segment 32 and the attached self expanding stent 45 at the delivery site 51 within the vessel 50 of the patient. Thereafter, the wire guide may be withdrawn or left in place. During this portion of the procedure, the thumbwheel 65 of the vascular intervention device delivery system 60 may be disabled by maintaining the lock 80 in its locked position as shown in FIG. 7. It is also important to note that when the vascular intervention device delivery system 60 is being maneuvered to a delivery site 51 (FIG. 3) the pin 55 is received in perimeter notch 46 of idler wheel 44 to prevent idler wheel 44 from rotating and to place the knurled surface 56 of pin 55 in contact with pull 38 to inhibit movement of retractable sheath 37 toward the proximal direction to uncover stent 45.

After the distal carrier segment 32 has arrived at and is properly positioned at delivery site 51, and it is now time to deploy the self expanding stent 45, the user may depress pusher 85 to disengage lock 80 and move latch 81 out of contact with the radially outward thumb surface 66 of thumbwheel 65. This movement of lock 80 also moves pin 55 out of perimeter notch 46 and out of contact with pull 38 as best shown in FIG. 11. This movement enables rotation of idler wheel 44. In addition, when pin 55 is moved out of contact with pull 38, the columnar support of pull 38 is relieved, and readies pull 38 to support tension as thumbwheel 65 is rotated to take up the pull 38 on spool 67.

A method of operating vascular intervention device delivery system 10, 60 includes rotating the thumbwheel 15, 65 in a reverse direction to wind pull 38 onto spool 17, 67 to build up tension in the retractable sheath 37 and pull 38 without moving the retractable sheath 37 relative to the distal carrier segment 32 of catheter 30. The "reverse direction" is clockwise in the view of FIG. 1 and counter-clockwise in the view of FIG. 7. In both cases, the "reverse direction" means that the user's thumb moves toward their palm to rotate the thumbwheel 15, 65. Next, a portion, which is less than all, of the distal carrier segment 32 is uncovered by continuing to rotate the thumbwheel 15, 65 in the reverse direction. At some point during the delivery procedure, the user may then pause rotation of the thumbwheel 15, 65 in the reverse direction. For instance, the user may pause in order to confirm that the vascular intervention device, such as a self expanding stent 45, is being delivered to the desired location in the vessel 50 of the patient. While the rotation of the thumbwheel 15, 65 is paused, tension in the pull 38 and the retractable sheath 37 is maintained by holding the ratchet 20, 70 and preventing rotation of the thumbwheel 15, 65 in the forward direction. Ratchet 20, 70 may be considered to be in a hold configuration when catches 23, 73 are received in one of the stops 25, 75 of the ratchet surface 21, 71. A remaining portion of the distal carrier segment 32 is then uncovered to facilitate complete deployment of the self expanding stent 45 by resuming rotation of the thumbwheel 15, 65 in the reverse direction until retractable sheath 37 arrives at its second position fully uncovering distal carrier segment 32.

An important aspect of the ratchet operated vascular intervention device delivery system 10, 60 of the present disclosure is to allow for rotation of thumbwheel 15, 65 in one direction only. This means that the pull 38 and hence the retractable sheath 37 can only be pulled proximally. If the thumbwheel 15, 65 were able to rotate in both directions, it could cause the pull 38 to slack and possibly jump out of the collection diameter of the spool 17, 67 on thumbwheel 15, 65. Also, by keeping the rotation of thumbwheel 15, 65 to one direction only, ratchet 20, 70 allows all of the energy already placed in the system 10, 60 by the user to be maintained. For example, if the user was to partially deploy a self expanding stent 45 that had a deployment force of 30N the user will have to put effort into getting the stent to partially deploy. This effort could have caused the sheath 37 to stretch slightly and also the inner catheter 30 to compress slightly. If this energy were lost when the thumbwheel 15, 65 were released, it would mean that when the deployment was resumed from that point, the user would have to rotate the thumbwheel 15, 65 an amount in order to reestablish tension in the system 10, 60 again before the self expanding stent 45 would continue to deploy. This may be especially important in the case of deploying longer stents that require higher forces.

It should be understood that the above description is intended for illustrative purposes only, and is not intended to limit the scope of the present disclosure in any way. Thus, those skilled in the art will appreciate that other aspects of the disclosure can be obtained from a study of the drawings, the disclosure and the appended claims.

What is claimed is:

1. A vascular intervention device delivery system comprising:
   a handle;
   a thumbwheel rotatably mounted in the handle and having a spool and a radially outward thumb surface;
   a catheter with a proximal end attached to the handle, and a distal carrier segment for mounting a vascular intervention device thereon;
   a retractable sheath movable from a first position covering the distal carrier segment to a second position retracted proximally uncovering the distal carrier segment; and
   a pull extending between the thumbwheel and the retractable sheath, and the pull having a cross sectional shape with a concave side that is opposite to a convex side, both of which are flanked by rounded edges;
   an idler wheel rotatably mounted in the handle at a location proximal to the thumbwheel; and
   wherein the pull wraps around the idler wheel to return in a direction for being wound onto the spool of the thumbwheel.

2. The vascular intervention device delivery system of claim 1 wherein one of the convex side and the concave side of the pull is in contact with the idler wheel; and
   an other of the convex side and the concave side of the pull is in contact with the spool.

3. The vascular intervention device delivery system of claim 2 wherein the idler wheel defines a perimeter notch;
   a pin movably mounted in the handle, and being movable between a first position and a second position;
   wherein the pin is received in the perimeter notch to block rotation of the idler wheel in the first position, but being outside the perimeter notch to permit rotation of the idler wheel at the second position.

4. The vascular intervention device delivery system of claim 3 wherein the pin has a knurled surface in contact with the pull in the first position; and
   the knurled surface is out of contact with the pull in the second position.

5. The vascular intervention device delivery system of claim 4 including a lock slidably positioned in the handle, and being movable between a locked position in contact with the thumbwheel and an unlocked position out of contact with the thumbwheel;
   the pin is attached to move with the lock.

6. The vascular intervention device delivery system of claim 1 wherein the thumbwheel includes a radially inward oriented ratchet surface of a ratchet;
   a ratchet pawl of the ratchet being mounted in the handle and having a catch in contact with the ratchet surface; and the ratchet locking the thumbwheel against rotation in a forward direction, and the retractable sheath moving responsive to rotation of the thumbwheel in a reverse direction.

7. The vascular intervention device delivery system of claim 6 wherein the idler wheel defines a perimeter notch;
a pin movably mounted in the handle, and being movable between a first position and a second position;
wherein the pin is received in the perimeter notch to block rotation of the idler wheel in the first position, but being outside the perimeter notch to permit rotation of the idler wheel at the second position.

8. The vascular intervention device delivery system of claim 7 including a lock slidably positioned in the handle, and being movable between a locked position in contact with the thumbwheel and an unlocked position out of contact with the thumbwheel; and
the pin is attached to move with the lock;
wherein the pin is in contact with the pull in the first position; and
the pin is out of contact with the pull in the second position.

9. A vascular intervention device delivery system comprising:
a handle;
a thumbwheel rotatably mounted in the handle and having a spool and a radially outward thumb surface;
a catheter with a proximal end attached to the handle, and a distal carrier segment for mounting a vascular intervention device thereon;
a retractable sheath movable from a first position covering the distal carrier segment to a second position retracted proximally uncovering the distal carrier segment; and
a pull extending between the thumbwheel and the retractable sheath;
an idler wheel rotatably mounted in the handle at a location proximal to the thumbwheel, and the idler wheel defines a perimeter notch;
a pin movably mounted in the handle, and being movable between a first position at which the pin is received in the perimeter notch to block rotation of the idler wheel, and a second position outside the perimeter notch to permit rotation of the idler wheel; and
wherein the pull wraps around the idler wheel to return in a direction for being wound onto the spool of the thumbwheel.

10. The vascular intervention device delivery system of claim 9 including a lock slidably positioned in the handle, and being movable between a locked position in contact with the thumbwheel and an unlocked position out of contact with the thumbwheel; and
the pin is attached to move with the lock.

11. The vascular intervention device delivery system of claim 10 wherein the pin is in contact with the pull in the first position; and
the pin is out of contact with the pull in the second position.

12. The vascular intervention device delivery system of claim 11 including a stability sheath;
the pull is positioned between the catheter and the stability sheath, and the pull has a cross sectional shape with a convex side in contact with the stability sheath and a concave side.

13. The vascular intervention device delivery system of claim 12 wherein the pull is a metallic band with a curved cross section.

14. The vascular intervention device delivery system of claim 9 wherein the thumbwheel includes a radially inward ratchet surface of a ratchet;
a ratchet pawl of the ratchet being mounted in the handle and having a catch in contact with the ratchet surface; and
the ratchet locking the thumbwheel against rotation in a forward direction, and the retractable sheath moving responsive to rotation of the thumbwheel in a reverse direction.

15. The vascular intervention device delivery system of claim 14 including a stability sheath;
the pull is positioned between the catheter and the stability sheath, and the pull has a cross sectional shape with a convex side in contact with the stability sheath and a concave side;
wherein the pull is a metallic band with a curved cross section.

16. The vascular intervention device delivery system of claim 15 including a lock slidably positioned in the handle, and being movable between a locked position in contact with the thumbwheel and an unlocked position out of contact with the thumbwheel;
the pin is attached to move with the lock;
wherein the pin has a knurled surface in contact with the pull in the first position; and
the knurled surface is out of contact with the pull in the second position.

17. A method of operating a vascular intervention device delivery system that includes a thumbwheel rotatably mounted in the handle and having a radially outward thumb surface; a catheter with a proximal end attached to the handle, and a distal carrier segment for mounting a vascular intervention device thereon; a retractable sheath movable from a first position covering the distal carrier segment, and a second position retracted proximally uncovering the distal carrier segment; a pull extending between the thumbwheel and the retractable sheath; an idler wheel rotatably mounted in the handle at a location proximal to the thumbwheel, and the idler wheel defines a perimeter notch; a pin movably mounted in the handle, and being movable between a first position at which the pin is received in the perimeter notch to block rotation of the idler wheel, and a second position outside the perimeter notch to permit rotation of the idler wheel, wherein the pull wraps around the idler wheel to return in a direction for being wound onto the spool of the thumbwheel, and the method comprising the steps of:
inhibiting movement of the retractable sheath toward the second position while a distal carrier segment of the vascular intervention device delivery system is being maneuvered to a delivery site at least in part by contacting the pull with a pin mounted in the handle;
moving the pin out of contact with the pull when the distal end arrives at the delivery site;
moving the retractable sheath from the first position to the second position responsive to rotation of the thumbwheel in a reverse direction.

18. The method of claim 17 including blocking rotation of the idler wheel during the inhibiting step at least in part by receiving the pin in a notch defined by the idler wheel; and
wherein the step of moving the pin includes moving the pin out of the notch to enable rotation of the idler wheel.

19. The method of claim 18 including contacting one of the convex side and the concave side of the pull with the idler wheel; and contacting an other of the convex side and the concave side of the pull with the spool.

20. The method of claim 19 including rotating the thumbwheel in the reverse direction to build up tension in the pull without moving the retractable sheath relative to the distal carrier segment of the catheter;
   pausing rotation of the thumbwheel in the reverse direction;
   maintaining tension in the pull by locking a ratchet and preventing rotation of the thumbwheel in the forward direction.

\* \* \* \* \*